United States Patent [19]

Iglesias

[11] 4,068,667
[45] Jan. 17, 1978

[54] ANTI-ARCING RESECTOSCOPE

[76] Inventor: Jose J. Iglesias, 1341 North Ave., Elizabeth, N.J. 07200

[21] Appl. No.: 720,424

[22] Filed: Sept. 3, 1976

[51] Int. Cl.² .............................................. A61B 17/32
[52] U.S. Cl. ............................................... 128/303.15
[58] Field of Search ....................... 128/303.13–303.17, 128/407–409

[56] References Cited

U.S. PATENT DOCUMENTS

| 3,850,175 | 11/1974 | Iglesias | 128/303.15 |
| 3,939,839 | 2/1976 | Curtiss | 128/303.15 |
| 3,939,840 | 2/1976 | Storz | 128/303.15 |

FOREIGN PATENT DOCUMENTS

| 1,020,980 | 2/1953 | France | 128/303.14 |
| 2,502,863 | 7/1976 | Germany | 128/303.15 |

Primary Examiner—John D. Yasko
Assistant Examiner—Lee S. Cohen
Attorney, Agent, or Firm—Scrivener, Parker, Scrivener & Clarke

[57] ABSTRACT

A resectoscope used in performing transurethral operations has a telescope extending longitudinally of the instrument which is supported and stabilized by an elongated metallic tube which at its proximate end is fixed to the block of the electrotome. In accordance with the invention the distal end of the tube is extended beyond the distal end of the telescope sufficiently that there will be no interference with illumination through the telescope and the distal end of the tube is coated for a substantial distance from its extreme distal end with a material which is nonconductive to electricity, resistant to high temperatures and chemicals used in transurethral procedures, and provides an antifriction surface on a surface to which it adheres.

2 Claims, 3 Drawing Figures

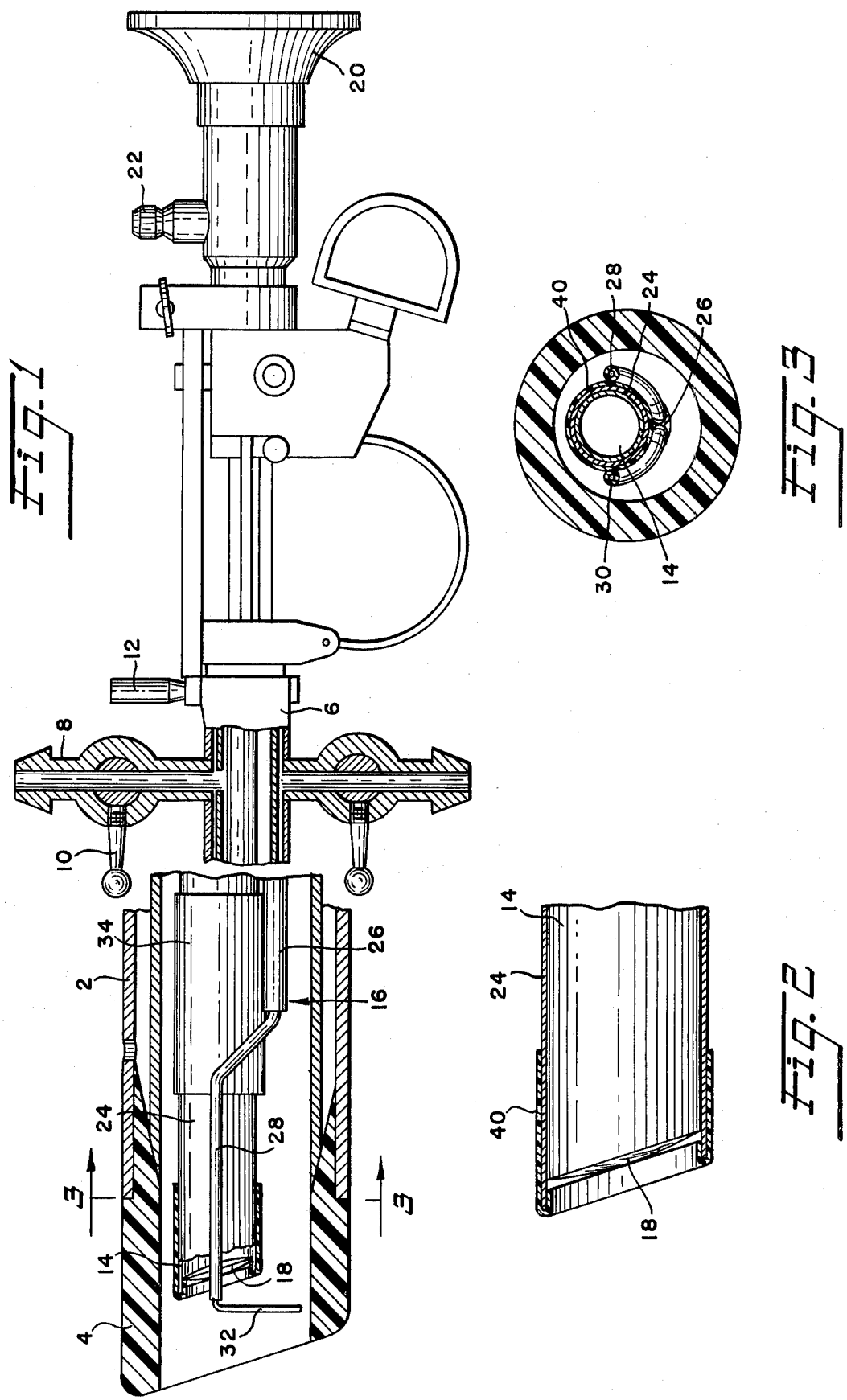

ANTI-ARCING RESECTOSCOPE

BACKGROUND OF THE INVENTION

A resectoscope having parts of conventional construction is disclosed in FIG. 1 as background for disclosure of the invention, and comprises a metallic tubular sheath 2 which provides a passageway through the human urethra to the area of visual and operative interest, and which has at its distal end a beak 4 which is formed of an electrically insulating material such as a synthetic plastic. At its proximate end the sheath is attached to a metallic block 6 at which there is a tube 8 with stopcock 10 for the introduction of clear irrigating fluid, and a thumb screw 12 for attaching the sheath's metallic socket the the block 6 which activates the cutting loop assembly and electrode in performing an operation.

Within the sheath are the telescope 14 and the cutting loop assembly 16. The telescope has an objective lens 18 at its distal end and an ocular lens (not shown) and eyepiece 20 at its proximal end. Fiberglass light conductors (not shown) extend through the telescope from an external connection 22 to the distal end for providing illumination. The telescope is supported and stabilized within the sheath by an elongated metallic tube 24 which partially or entirely surrounds the telescope in tight engagement. This tube is connected at its proximal end to the block 6 and in all resectoscopes prior to this invention its distal end is positioned proximal to the distal end of the telescope.

The cutting loop assembly 16 comprises, in one of its conventional forms, the elongated hollow stem 26 which extends along and beneath the telescope stem and through which a wire passes which protrudes from the distal end of the stem to form two parallel arms 28, 30 which are insulated and are positioned on opposite sides of the telescope tube 24 adjacent its distal end and which are connected at their distal ends by a depending semicircular bare wire cutting loop 32 which is activated by high frequency electrical energy and is used to resect pathological tissues and coagulate bleeding vessels. The stem 26 transmits the reciprocating movement of the working element to the cutting loop 32, and the wire in the stem and arms 28, 30 transmits high frequency electrical energy to the cutting loop 32. A tube 34 is connected to the distal end of the stem 26, and is positioned between the arms 28, 30 and slidably surrounds the tube 24 in order to provide support to the cutting loop 16.

In performing an operative procedure using the resectoscope, electrical arcing between the un-insulated distal ends of the arms, or the upper ends of the cutting loop, and the adjacent distal end of the telescope often occurs when the cutting loop assembly is moved to rest position and the end of the telescope is touched either by a piece of incompletely resected tissue which has adhered to the cutting loop or by the wire of a broken or deformed cutting loop. This arcing may damage the telescope, adversely affect the operative procedure and injure the surgeon, or both. There have been many reports in the literature of eye injury to surgeons while performing transurethral operations, and it is well known that most surgeons have experienced electrical shocks and burning of the hand, cheek, nose and ears caused by arcing during performance of an operation with the use of the resectoscope. Among the methods suggested to correct this difficulty are (1) positioning the distal end of the telescope proximally within the sheath beyond the position of optimum vision, (2) reducing the proximal movement of the cutting loop assembly in order to maintain the bare wire cutting loop at a safe distance from the telescope, and (3) extending the insulation of the spaced parallel arms of the cutting loop assembly over and beyond the junction of the arms and depending loop. None of these have been satisfactory as none have completely prevented arcing, and the object of my present invention has been to prevent arcing while at the same time maintaining the increased illumination and field of vision provided by modern telescopes of resectoscopes, without interference with the endoscopic field of vision and without decreasing the endoscopic operative field vision and the capacity of resection at each stroke of the cutting loop.

SUMMARY OF THE INVENTION

In a resectoscope the metal tube which partially or completely surrounds the telescope and supports and stabilizes it is extended at its distal end beyond the distal end of the telescope, and the distal end of the tube is coated with a material which is non-conductive to electricity, resistant to high temperatures and chemicals used in transurethral procedures, and provides an anti-friction surface on a surface to which it adheres.

DESCRIPTION OF THE DRAWINGS

FIG. 1 is a side view of a resectoscope, being partially broken away and partially enlarged and in section to illustrate the present invention;

FIG. 2 is an enlarged view of the distal end of the telescope and surrounding tube, showing the coating applied thereto in accordance with the invention, and FIG. 3 is a sectional view taken on line 3—3 of FIG. 1.

DESCRIPTION OF THE INVENTION

In accordance with the invention, and as disclosed in the drawings, the distal end of the tube 24 which supports and at least partially surrounds the telescope is extended at its distal end beyond the distal end of the telescope, and the distal end of this tube is completely covered with a layer of material 40 which is nonconductive to electricity, resistant to high temperatures and chemicals used in transurethral procedures, and provides an anti-friction surface on a surface to which it adheres. The purpose of the extension of tube 24 and the coating material is to prevent electrical arcing between the bare wire cutting loop 32 and the telescope when the cutting loop is in its most retracted position, and it has been found that good results are obtained if the tube 24 is extended approximately 0.5 mm. beyond the distal end of the telescope and the coating is continued for approximately one inch in a direction proximal to the distal end of the tube 24.

Any material having the foregoing described characteristics may be used as the coating material, and I have found that the Teflon provides satisfactory results.

I claim:

1. A resectoscope comprising an elongated tubular sheath having a distal end, an elongated tubular telescope within and extending longitudinally of the sheath and having a distal end adjacent the distal end of the sheath, a tube extending longitudinally of the sheath and the telescope and having a distal end adjacent the distal end of the telescope and at least partially surrounding and engaging the telescope to support and stabilize it, and a cutting loop assembly mounted within the sheath for longitudinal reciprocation with respect to the telescope and the tube and having a depending bare wire loop disposed distally to the distal end of the telescope and the distal end of the tube and adapted to be charged with electricity, means for reciprocating the cutting loop assembly, the distal end of the tube extending beyond the distal end of the telescope and having its peripheral surface completely coated at and adjacent to its distal end with a material which is non-conductive to electricity, resistant to high temperatures and chemicals used in transurethral procedures, and provides an anti-friction surface on the surface of the tube on which it is coated.

2. A resectoscope according to claim 1, in which the tube extends at least 0.5 mm. beyond the distal end of the telescope.

* * * * *